United States Patent
Wang et al.

(10) Patent No.: US 8,231,027 B2
(45) Date of Patent: *Jul. 31, 2012

(54) VACUUM CONTAINER HAVING AIR RELEASE VALVE COVER

(76) Inventors: Jui Te Wang, Tichang Hsien (TW); Jordan S. Tarlow, Venice, CA (US)

(*) Notice: Subject to any disclaimer, the term of this patent is extended or adjusted under 35 U.S.C. 154(b) by 843 days.

This patent is subject to a terminal disclaimer.

(21) Appl. No.: 12/247,889

(22) Filed: Oct. 8, 2008

(65) Prior Publication Data
US 2009/0120939 A1   May 14, 2009

Related U.S. Application Data

(63) Continuation-in-part of application No. 11/983,503, filed on Nov. 9, 2007, now abandoned.

(51) Int. Cl.
| | |
|---|---|
| B65D 51/16 | (2006.01) |
| B65D 43/03 | (2006.01) |
| B65D 81/20 | (2006.01) |
| B65B 31/04 | (2006.01) |
| A47G 29/00 | (2006.01) |
| B65D 41/06 | (2006.01) |

(52) U.S. Cl. ........ 220/361; 220/380; 220/231; 220/293; 215/262; 211/71.01; 206/524.8; 141/65

(58) Field of Classification Search .......... 220/756, 220/203.04, 203.09, 203.23, 203.24, 293, 220/89.1, 367.1, 300, 231; 211/71.01, 74, 211/59.4; 206/524.8; 215/332, 262
See application file for complete search history.

(56) References Cited

U.S. PATENT DOCUMENTS

| | | | | | |
|---|---|---|---|---|---|
| 1,216,869 | A | * | 2/1917 | Snigo | 220/656 |
| 5,370,245 | A | * | 12/1994 | Tersch et al. | 211/74 |
| 5,397,024 | A | * | 3/1995 | Wu et al. | 220/231 |
| 5,697,510 | A | * | 12/1997 | Wang et al. | 215/262 |
| 6,523,459 | B1 | * | 2/2003 | Chameroy et al. | 99/337 |

* cited by examiner

Primary Examiner — Robin Hylton (57) ABSTRACT

A cover for a container fits with a sliding air tight fit over the container body. A cover air release valve allows escape of air from the container when removing and installing the cover to create a vacuum seal fit. A handle positioned adjacent to the air release valve enables a user to remove and install the cover with a single hand gripping the handle and pressing the air release valve. Protrusions extending from opposite sides of the container sleeve engage mating L-shaped openings in a bottom edge of the cover to lock the cover in place. Special dual sided cradles engage a top of a vacuum sealed container below each cradle and a bottom of a vacuum sealed container above each cradle so that a series of cradles are used to vertically stack a number of vacuum sealed containers.

7 Claims, 9 Drawing Sheets

VACUUM CONTAINER HAVING AIR RELEASE VALVE COVER

CROSS-REFERENCE TO RELATED APPLICATIONS

The present utility patent application is a continuation-in-part of U.S. patent application Ser. No. 11/983,503, filed Nov. 9, 2007.

STATEMENT REGARDING FEDERALLY SPONSORED RESEARCH OR DEVELOPMENT

Not Applicable.

THE NAMES OF THE PARTIES TO A JOINT RESEARCH OR DEVELOPMENT

Not Applicable.

BACKGROUND OF THE INVENTION

1. Field of the Invention

The present invention relates to a cover, and more particularly to a cover fit onto a container with a sliding air tight fit, the cover having an air release valve to allow escape of air from the container when the cover is pressed onto the container with the air release valve held open during the installation to release air from the container to create a vacuum seal with at least a partial vacuum in the container with the cover fully installed on the container with a tight vacuum seal fit and the cover only releasable for removal by opening the air release valve to admit air back into the container to break the vacuum seal and allow a user to slide the cover off with the air release valve held open.

2. Description of Related Art Including Information Disclosed Under 37 CFR 1.97 and 1.98

Closed containers keep items fresher within the container with a vacuum or partial vacuum within the container so that there is less air in the container to cause contained items to spoil, thereby preventing or prolonging spoilage. Prior art containers fail to provide a simple vacuum closure with a sliding cover rather than a threaded cover and a simple air release valve rather than a vacuum pump.

The closest prior art of which applicants are aware is their prior U.S. Pat. No. 5,397,024 to Wu et al. The cover includes a valve depressible inward of the cover for allowing air to flow inward or outward of the cover. However, the valve assembly includes a screw secured to the plug rod and engaged with the cover for preventing the valve assembly from disengaging from the cover. The screw is normally made of metal and may not be easily threaded into place. In addition, the screw which is made of metal material may not closely enclose the opening of the cover such that a rubber ring and a gasket are required to be engaged on the screw for engaging with the cover so as to enclose the opening. Furthermore, the inner thread of the plug rod may be easily damaged by the metal screw. The present invention has arisen to mitigate and/or obviate the afore-described disadvantages of the conventional covers for containers.

Another related prior art U.S. Pat. No. 5,697,510, issued Dec. 16, 1997 to Wang et al., provides a container including a cover engaged on an open top. A channel and an opening are formed in the cover. A knob is slidably engaged in the channel and includes a tube having a pair of shoulders. A plug has a pair of hooks engaged into the tube and engaged with the shoulders so as to secure the plug to the tube. A spring is biased between the knob and the plug for biasing the knob partially outward of the cover and for forcing the plug against the cover to enclose the orifice. The plug can be made of plastic material instead of metal material.

The prior art patents fail to provide a means for carrying the container or means for stacking a number of the containers or means for securely locking the cover on the container body.

What is needed is a cover fit precisely over a container with an air-tight sliding fit and an air release valve to create a vacuum seal fit with a vacuum or partial vacuum in the container by installing the cover thereon and a twist lock for the top with a top handle and adjacent air release valve to carry the container by the top handle.

BRIEF SUMMARY OF THE INVENTION

The primary object of the present invention is to provide a cover fit precisely over a container with an air-tight sliding fit and an air release valve to create a vacuum or partial vacuum in the container by installing the cover thereon.

A related object of the present invention is to provide a container cover with a cylindrical interior wall and a precisely matching cylindrical exterior face around a container opening to receive the cover, the cylindrical exterior face having a slightly angled truncated conical tapered upper portion with a smaller diameter adjacent to a top rim of the container opening and extending outwardly down to a straight vertical cylindrical surface spaced apart from the rim to allow the cover to slip easily over the rim down onto the mating cylindrical portion wherein the air release valve is required to install the cover over the outer cylindrical portion of the container sleeve.

Another object is to provide a cover and container further comprising a twist lock for the top with a top handle and adjacent air release valve to carry the container by the top handle.

An alternate object of the present invention is to provide a cover having a sliding vacuum fit on a container wherein an air release valve is positioned on a side of the cover adjacent to the top and the top of the cover is flat so that several covered containers can be stacked together.

A further object of the present invention is to provide a plurality of modular cradles for the containers to form a rack system for stacking a number of the vacuum sealed containers vertically.

Another objective of the present invention is to provide a cover of a container which includes no screw therein.

In brief, a cover for a container fits with a sliding air tight fit over the container body with an inner cover sleeve adjacent to the cover opening forming an air tight slidable fit with an outer container sleeve around the top opening of the container. The cover has an air release valve to allow escape of air from the container when the cover is pressed onto the container body with the air release valve held open during the installation to release air from the container to create a vacuum seal fit with at least a partial vacuum in the container with the cover fully installed on the container. The cover is only releasable for removal by opening the air release valve to admit air back into the container to break the vacuum and allow a user to slide the cover off with the air release valve held open. A handle positioned adjacent to the air release valve enables a user to remove and install the cover with a single hand gripping the handle and pressing the air release valve with a thumb of the same hand.

To further secure the cover at least a pair of protrusions extending from opposite sides of the container sleeve engage mating L-shaped openings in a bottom edge of the cover to lock the cover in place.

Special dual sided cradles engage a top of a vacuum sealed container below each cradle and a bottom of a vacuum sealed container above each cradle so that a series of cradles are used to vertically stack a number of vacuum sealed containers.

BRIEF DESCRIPTION OF THE SEVERAL VIEWS OF THE DRAWINGS

These and other details of the present invention will be described in connection with the accompanying drawings, which are furnished only by way of illustration and not in limitation of the invention, and in which drawings.

DETAILED DESCRIPTION OF THE INVENTION

In FIGS. 1-12, a vacuum sealed container 9 comprises a container body 10 including an open top 11 encircled by an outer body sleeve 12 and a cover 20 engaged on top of the container body 10 for enclosing the open top of the container body with a vacuum seal.

The cover 20 comprises an air release valve 30 in an upper portion of the cover above the container body and an interior cover sleeve 22 structured to mate with the outer body sleeve 12 with an airtight force fit over the mating outer body sleeve so that it is necessary to open the air release valve to slide the cover onto the container body releasing air through the air release valve 30 to create a vacuum seal, producing at least a partial vacuum in the container, with the cover fully installed on the container body as in FIGS. 2, 3, 5, 8, 10, and 12, and so that it is necessary to open the air release valve 30 to admit air into the container to release the vacuum seal to enable the cover 20 to be removed from the container body 10 as in FIGS. 1, 4, 9, and 11.

Figure 1:
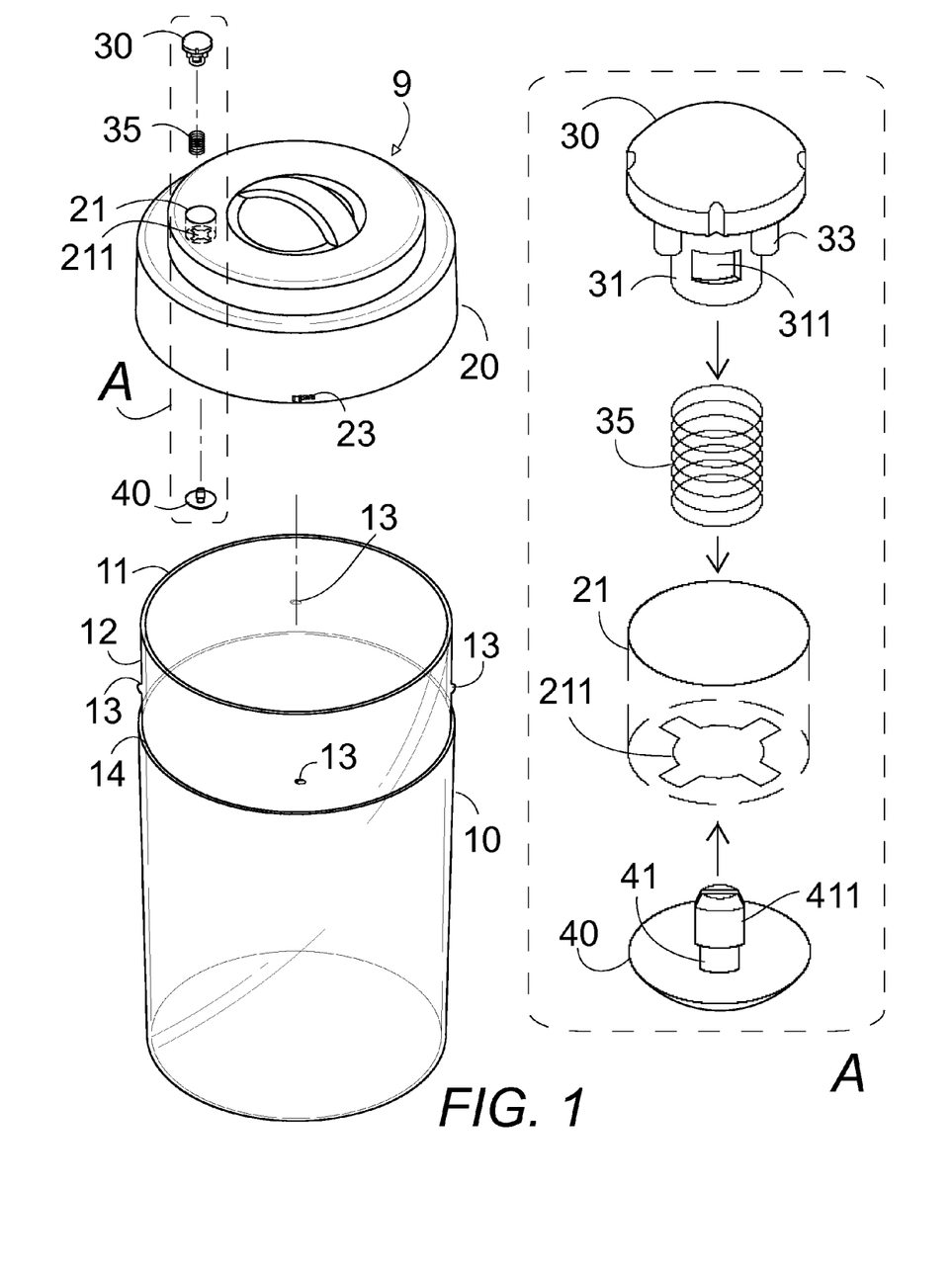
FIG. 1 is an exploded perspective view of the vacuum sealed container of the present invention with the container body, cover, and air release valve components all aligned for assembly.
Figure 2:
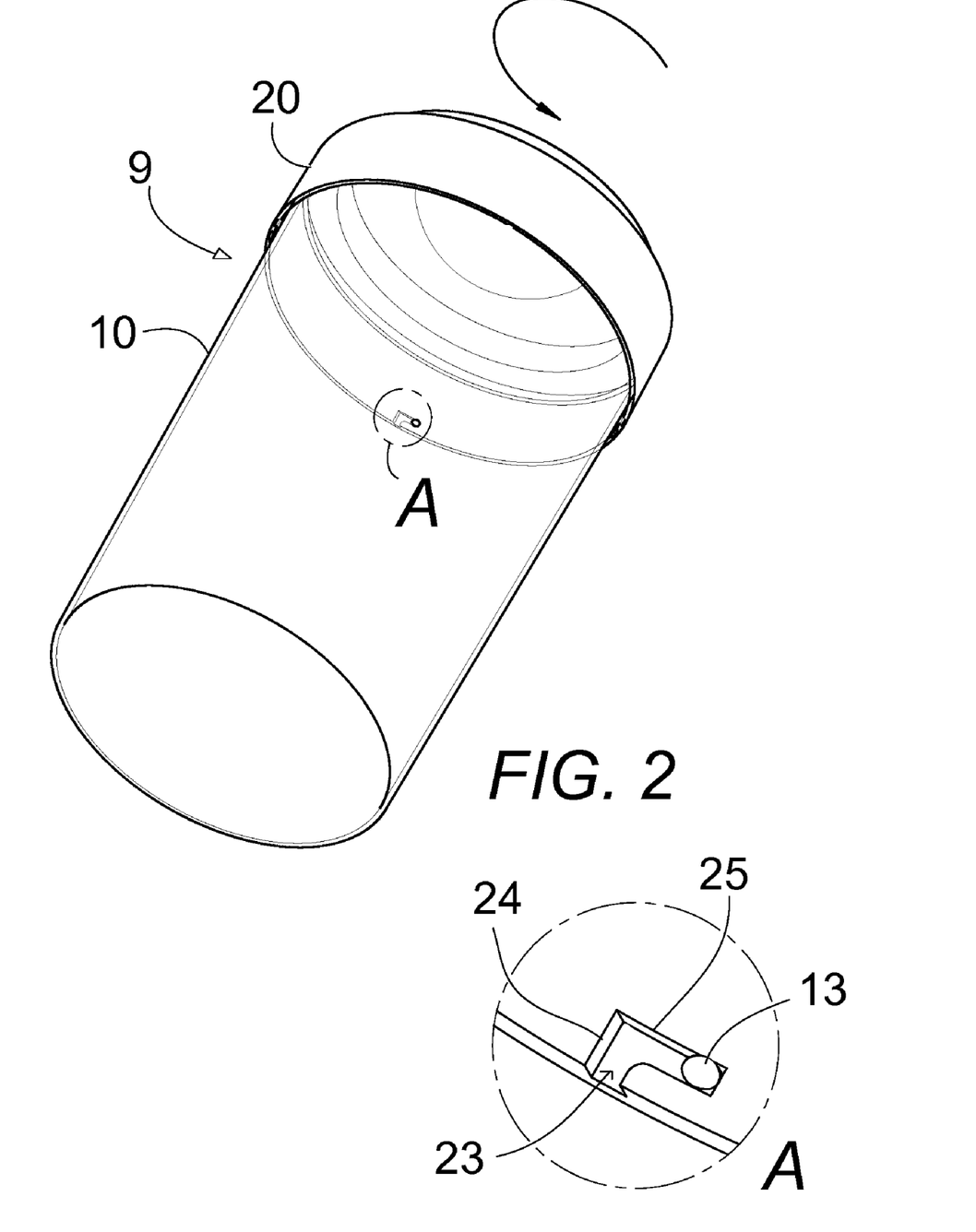
FIG. 2 is a perspective view of the vacuum sealed container of FIG. 1 with the cover on the container body showing the locking element.
Figure 3:
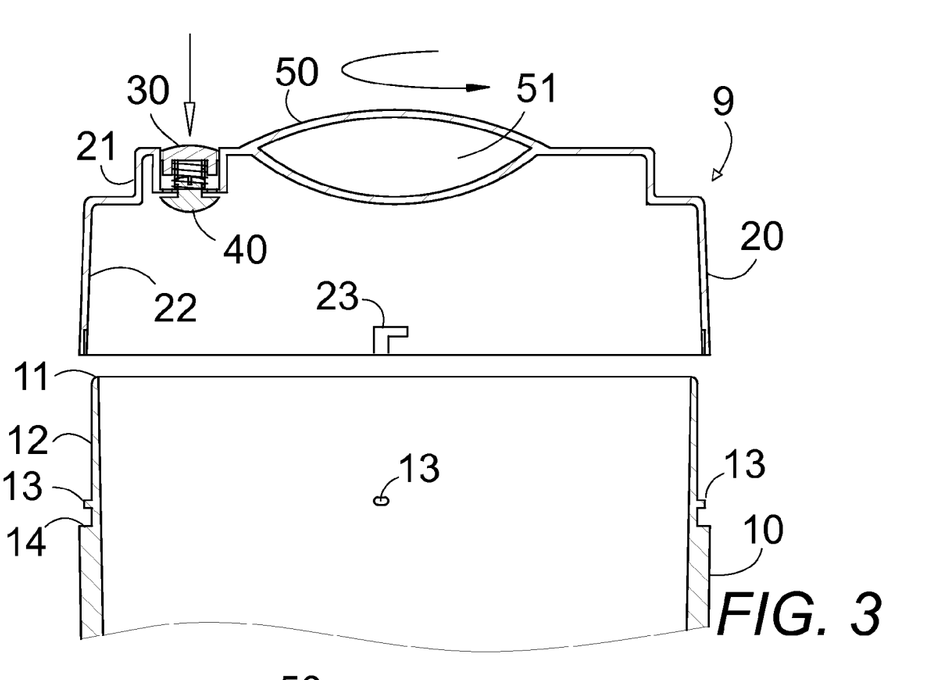
FIG. 3 is a partial cross sectional view of the vacuum sealed container of the present invention taken through 3-3 of FIG. 5 with the cover sealed on the container body.

In FIG. 1, exploded detail A, the air release valve with a knob 30 comprises a channel 21 formed in the cover and an air opening 211 formed through the cover, the opening communicating with the channel so that air can pass through the channel into the container. The knob 30 slidably engaged in the channel has a top portion normally protruding above the top of the cover for engaging the knob to activate the air valve, as shown in FIG. 3. A hollow tube 31 extends from the knob into the channel 21. The hollow tube has side wall openings 311. The knob 30 includes four projections 33 for engaging with the cover 20 so as to prevent the knob 30 from engaging into the channel 21 of the cover 20.

A bottom plug 40 engages the upper knob 30 through the air opening 211, the bottom plug having a flat top surface for covering the air opening to block the air. A shaft 41 extends upwardly from the bottom plug with an expanded partially tapered head 411 on the top of the shaft 41. The shaft 41 is inserted into the hollow tube 31 of the knob 30 and the head 411 snaps out into the side wall openings 311 to lock the bottom plug 40 to the knob 30 through the air opening 211 to allow the plug 40 to be quickly and easily secured to the knob 30. A coil spring 35 is engaged on the tube 31 and is biased between the knob 30 and the plug 40 so as to bias the knob 30 partially outward of the cover 20 and so as to force the plug 40 against the cover 20 for enclosing the orifice 211, as shown in FIG. 3, to normally seal the opening through the cover to prevent air from passing therethrough until the plug is pushed by a user to release the plug and admit the air through the opening.

Figure 4:
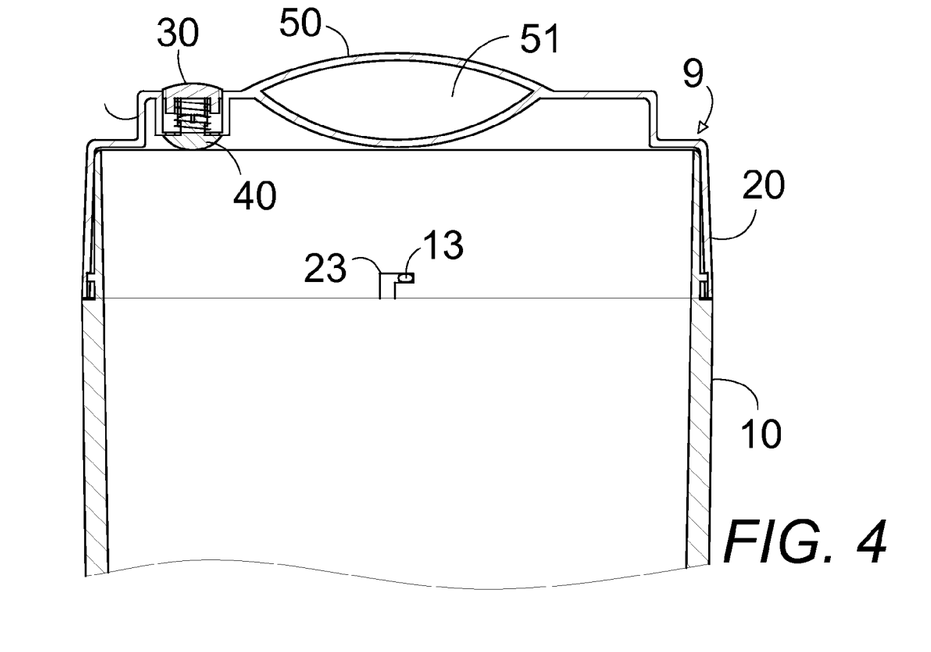
FIG. 4 is a partial cross sectional view of the vacuum sealed container of the present invention taken through 3-3 of FIG. 5 with the cover removed from the container body showing the combined pressing of the air release valve and the rotary motion of the cover to release the lock mechanism.
Figure 5:
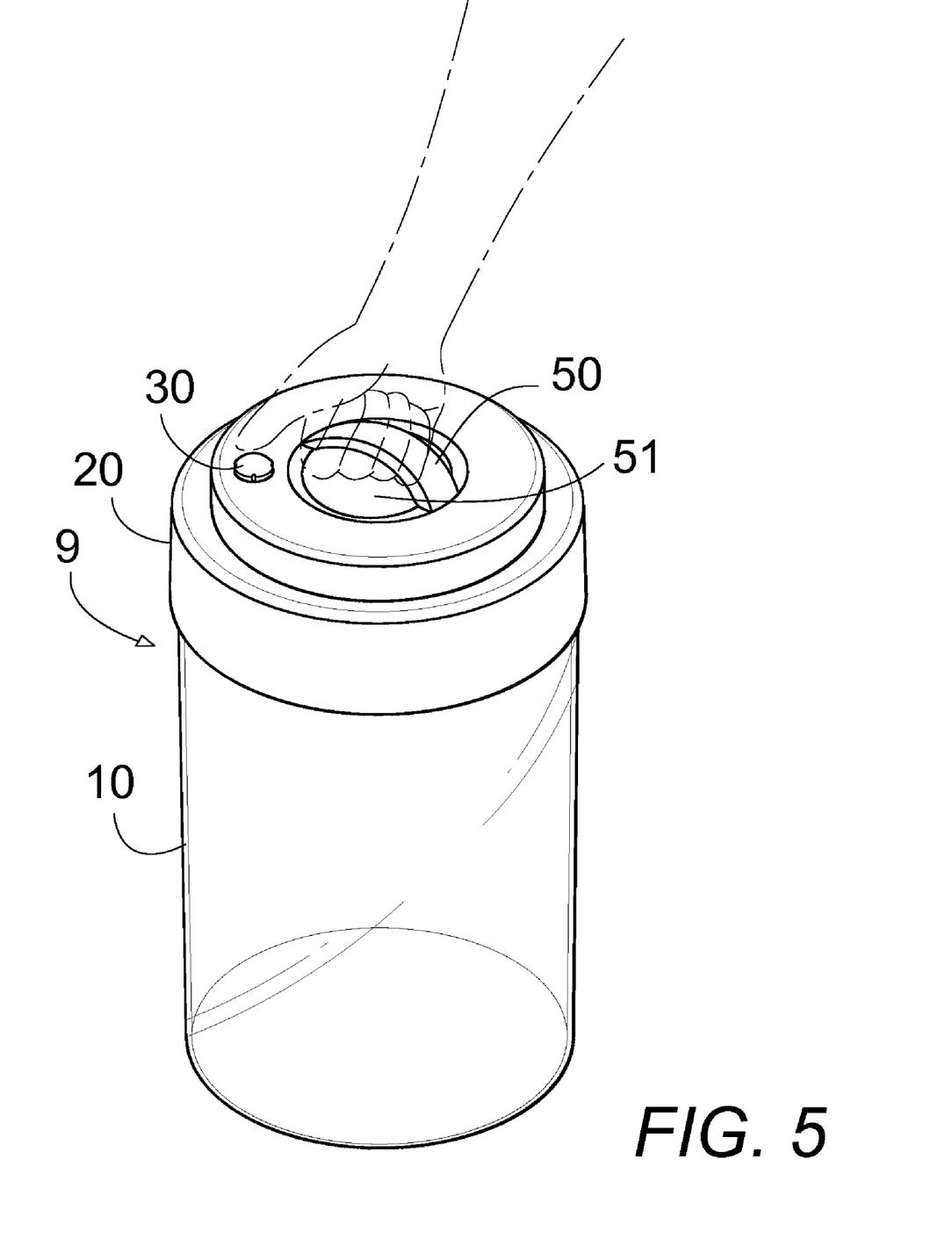
FIG. 5 is a perspective view of the vacuum sealed container of the present invention showing a hand of a user simultaneously gripping the handle and pressing the air release valve with a single hand.

In operation, as shown in FIG. 4, when the knob 30 is depressed inward of the channel 21, the plug 40 is disengaged from the opening 211 such that the opening 211 is opened and such that air is allowed to flow inward or flow outward of the cover.

It is to be noted that the plug 40 can be easily made by molding processes and can be made with plastic materials instead of metal material that is used for making the typical fastening screw. In addition, the plug 40 can be easily and quickly secured to the knob 30. Furthermore, the plug 40 itself is good enough to be used for closely enclosing the opening 211.

The biasing means biased between the knob and the plug for biasing the knob partially outward of the cover and for forcing the plug against the cover is preferably a spring 35 but may be a different type of biasing means.

The cover 20 is further locked onto the container body 10 by at least one protrusion 13 on a side of the outer body sleeve 12 interlocking with at least one mating L-shaped opening 23 on a bottom edge of the cover 20 to mate with the protrusion. As the cover 20 is installed on the container body 20, while activating the air release valve 30, a vertical edge portion 24 of each of the L-shaped openings 23 engages the mating protrusion 13 and as the protrusion reaches a horizontal portion 25 of the L-shaped opening 23 the cover is turned to fully insert the protrusion in the horizontal portion to lock the cover 20 onto the container 10 to enable the container to be lifted by the cover, as in FIG. 5. The cover 20 is turned in an alternate direction to align the vertical edge portion 24 of the L-shaped opening 23 with the protrusion 13 and the cover lifted while activating the air release valve 30 to remove the cover 20 from the container body 10, as shown in FIG. 4.

A handle 50 extends out from the top of the cover 20 with a gripping space 51 between the handle 50 and the cover to grip the handle to maneuver the cover 20 onto and off of the container body 1O. The handle 50 is positioned adjacent to the air release valve 30 so that the air release valve 30 may be activated by a hand of a user holding the handle 50, as in FIG. 5 with the finger's of the user around the handle and the thumb of the user pushing the air release valve 30. The handle 50 on the cover 20 is also used to lift the container with the cover locked on, as in FIG. 5.

Figure 6:
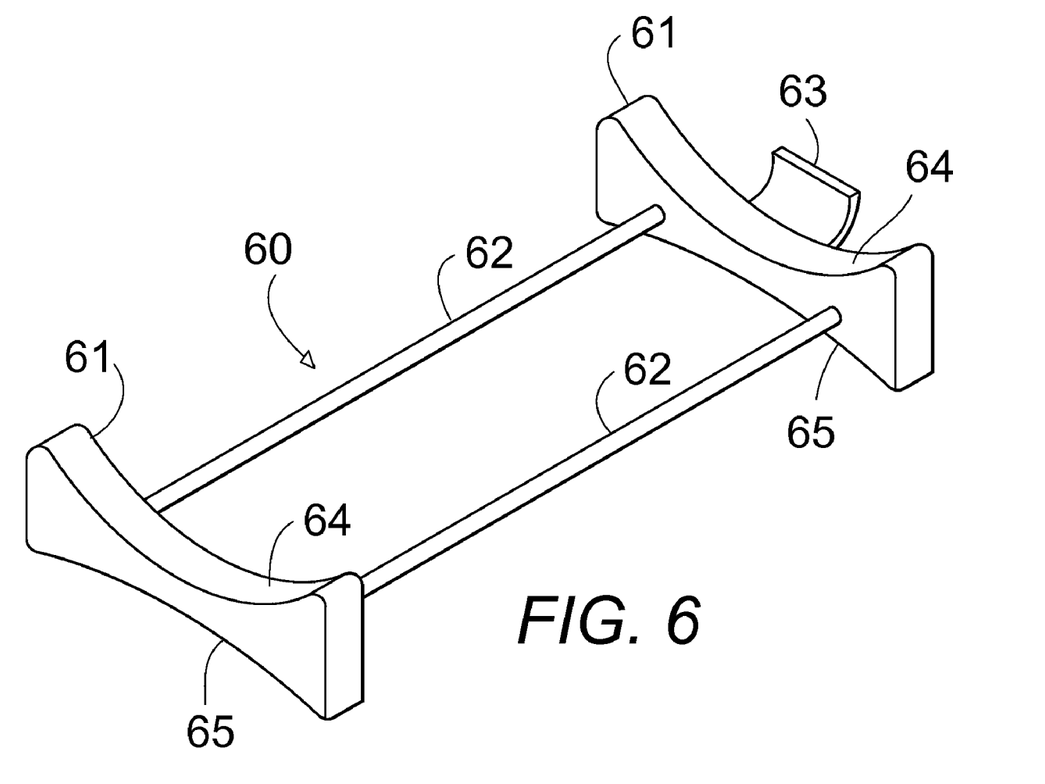
FIG. 6 is a perspective view of one of the cradles of the stacking system of the present invention used for stacking a vertical array of the vacuum sealed containers of the present invention.
Figure 7:
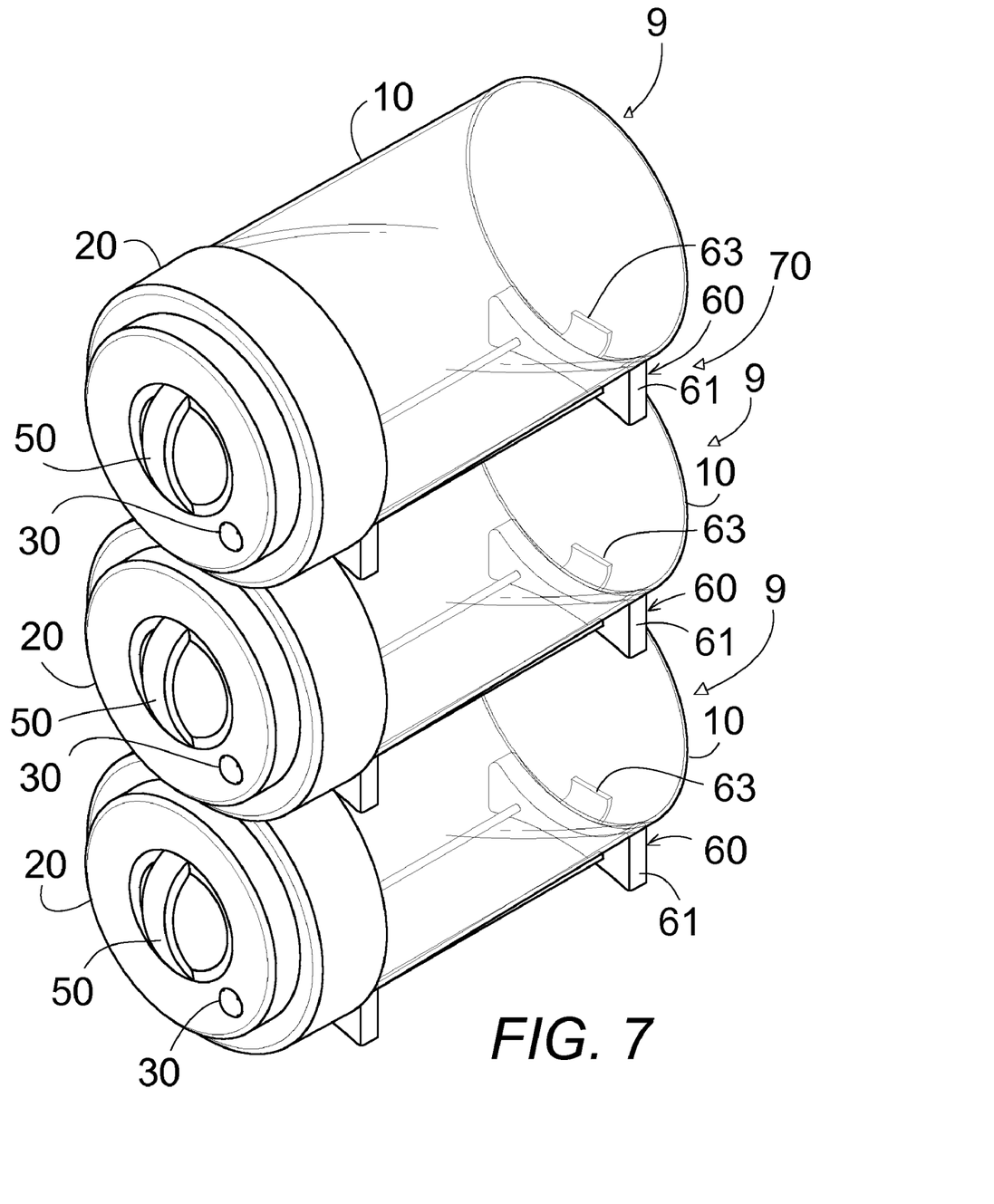
FIG. 7 is a perspective view of a stacked vertical array of the vacuum sealed containers of the present invention using the cradles of FIG. 6.

In FIGS. 6 and 7, the vacuum sealed container 9 further comprises a rack 70 for vertically stacking a plurality of the vacuum sealed containers, as in FIG. 7, with each oriented horizontally in a vertical stacked array. The rack 70 comprises a plurality of container supports 60, each container support 60 comprising a pair of horizontally spaced mating cradles 61 interconnected by a pair of dowels 62 or other means for rigidly interconnecting the cradles 61. Each of the cradles 61 comprises an elongated member having a top surface 64 for engaging and supporting a bottom of a vacuum sealed container 9 and a bottom surface 65 for resting on a top of a vacuum sealed container 9 so that a container support is positioned under a bottom vacuum sealed container and between each adjacent vacuum sealed container in the vertical stacked array, as shown in FIG. 7.

Each of the container supports further comprises a container edge support 63 protruding from a back edge of one of the cradles 61. The container edge support 63 configured to receive and support a bottom edge of one of the vacuum sealed containers to prevent each vacuum sealed container 9 from sliding off a back of the stacked array, as in FIG. 7, so that the covers 20 may be installed on and removed from the container bodies 10 to access contents of the vacuum sealed containers 9 while remaining in the vertical stacked array.

Figure 8:
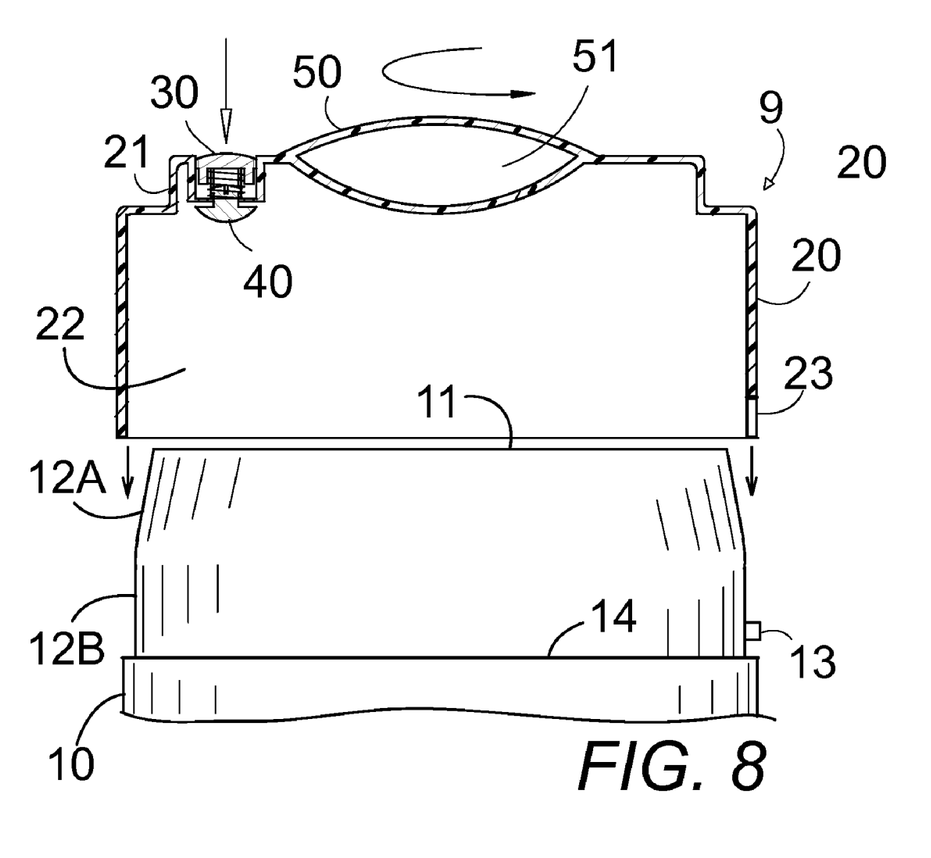
FIG. 8 is a perspective view of an alternate embodiment of the vacuum sealed container of the present invention having a flat topped cover with the vacuum release valve on the side of the cover adjacent to the top.

In FIG. 8, the cover of FIG. 1 has a top handle 50 and top pressure release button 30. The cover is aligned for installation on a container 10A having a tapered conical upper portion 12A of the cylindrical sleeve around the top opening rim 11 of the container 10A to allow the cover 20 to slip easily over the rim 11 down past the tapered conical upper portion 12A onto the mating cylindrical portion 12B wherein the air release valve 30 is required to install the cover over the outer cylindrical portion 12B of the container sleeve.

Figure 9:
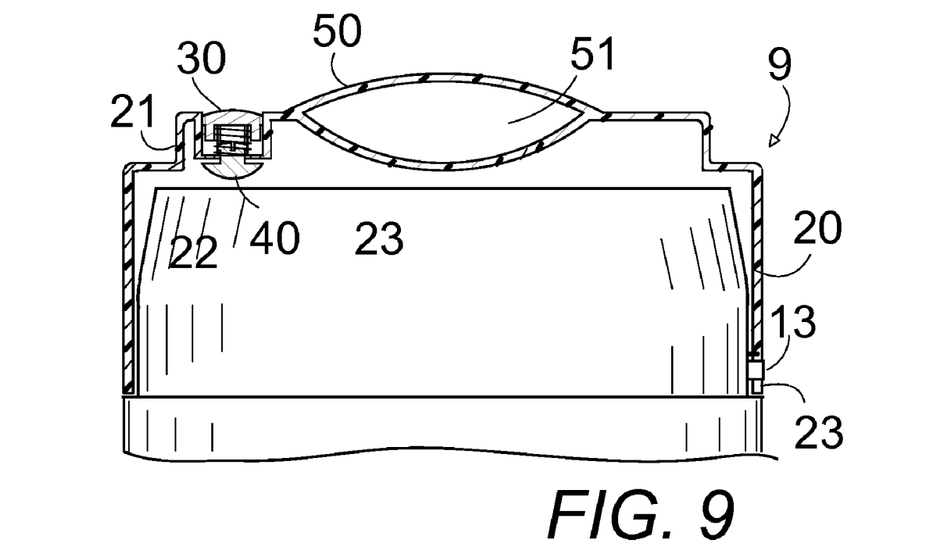
FIG. 9 is a partial cross-sectional view of the cover of FIG. 8 aligned for installation on a container having a tapered conical upper portion of the cylindrical sleeve around the top opening of the container.

In FIG. 9 the cylindrical cover 20 of FIG. 8 is installed on the container 10 having the tapered conical upper portion 12A of the cylindrical sleeve 12B.

Figure 10:
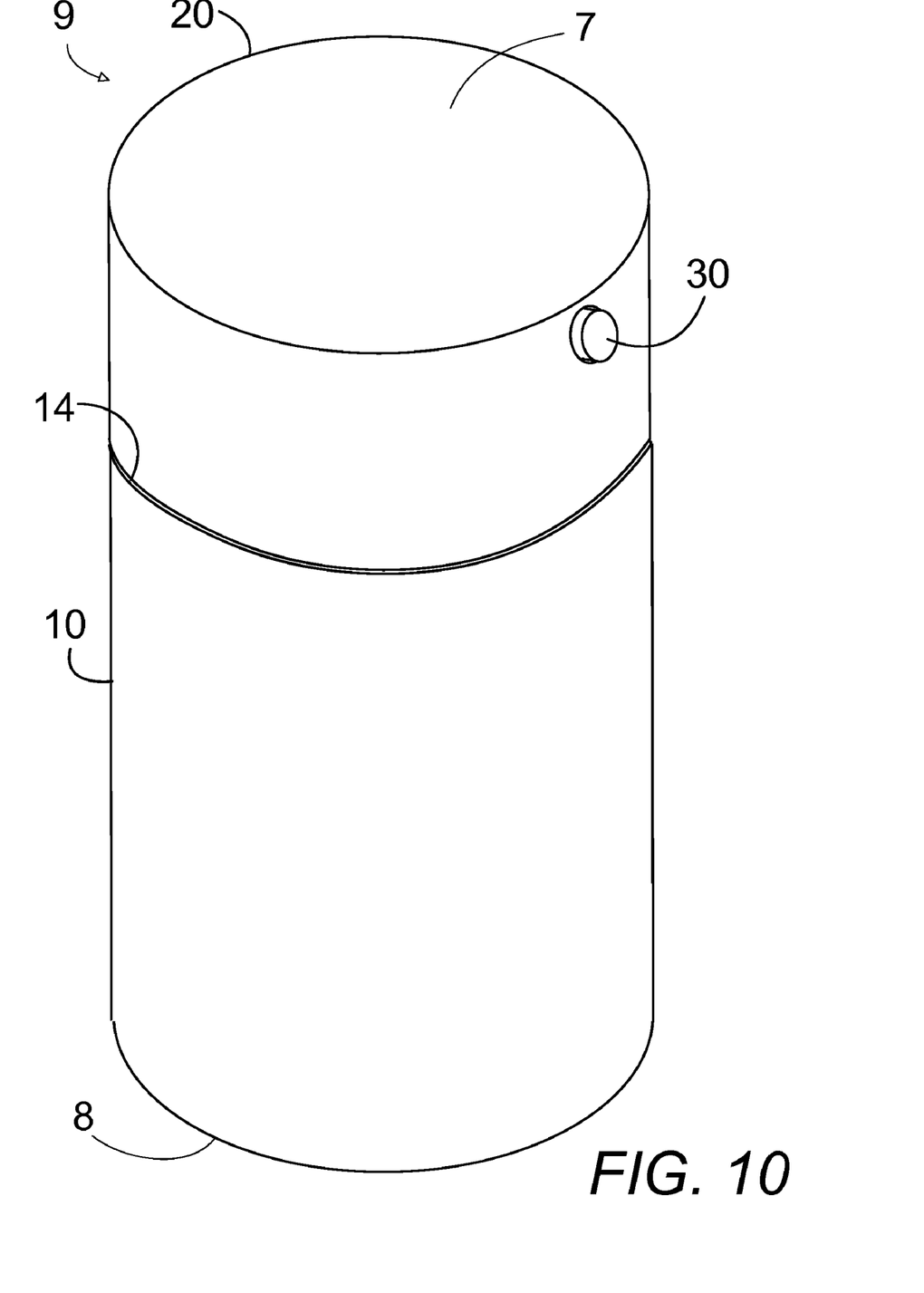
FIG. 10 is a partial cross-sectional view of the cylindrical flat top cover of FIG. 8 installed on the container having a tapered conical upper portion of the cylindrical sleeve around the top opening of the container.

In FIG. 10, an alternate embodiment of the vacuum sealed container 9A of the present invention has a vacuum release valve 30 on the side of the cover 20A adjacent to the top and a flat top surface 7 so that the covered containers may be stacked on top of each other with a bottom 8 of one container 10 resting on a top 7 of the cover 20 of another covered container 9A.

Figure 11:
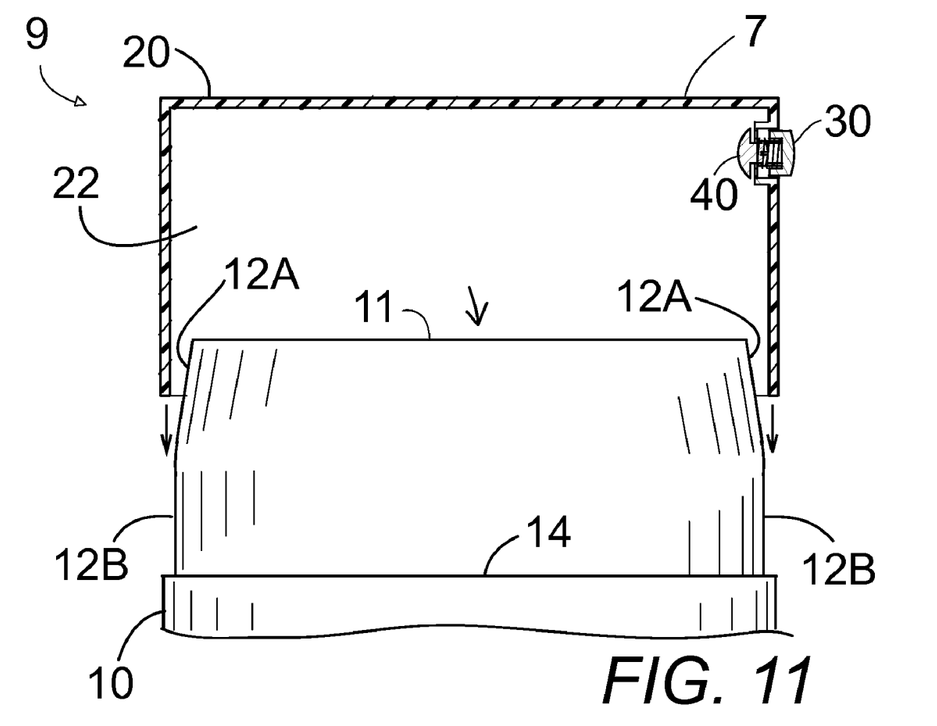
FIG. 11 is a partial cross-sectional view of the cover of FIG. 1 having a top handle and top pressure release button, the cover aligned for installation on a container having a tapered conical upper portion of the cylindrical sleeve around the top opening of the container.

In FIG. 11, the cover 20A of FIG. 10 is aligned for installation on a container 10A having a tapered conical upper portion 12A of the cylindrical sleeve 12B around the top opening rim 11 of the container 10A to allow easy insertion of the container cover 20A with a cylindrical interior wall 22 and a precisely matching cylindrical exterior cylindrical sleeve 12B around the container opening to receive the cover. The exterior face cylindrical sleeve 12B has a slightly angled truncated conical tapered upper portion 12A with a smaller diameter adjacent to a top rim 11 of the container opening and expanding outwardly down to a straight vertical cylindrical surface 12B spaced apart from the rim 11 to allow the cover to slip easily over the rim 11 down over the tapered upper portion 12A onto the mating cylindrical portion 12B wherein the air release valve is required to install the cover over the outer cylindrical portion of the container sleeve.

Figure 12:
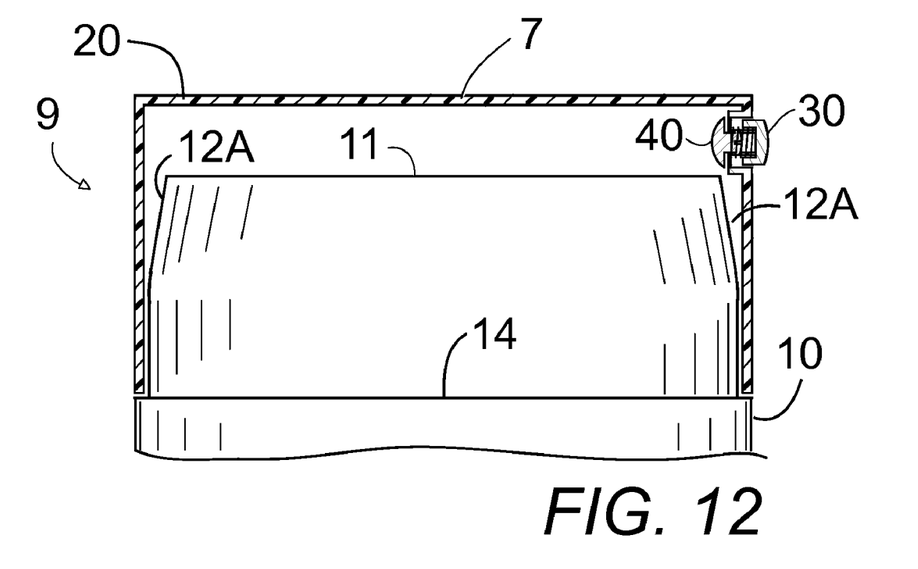
FIG. 12 is a partial cross-sectional view of the cylindrical cover of FIG. 1 having a top handle and top pressure release button, the cover installed on the container having a tapered conical upper portion of the cylindrical sleeve around the top opening of the container.

In FIG. 12, the flat top cover of FIG. 10 is installed over the container sleeve.

The vacuum sealed containers 9 may be made in a variety of sizes including large 10 liter size containers to house any desired contents to maintain the contents in a fresh condition due to the vacuum seal.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

What is claimed is:

1. A vacuum sealed container comprising:
 a container body including an open top encircled by an outer body sleeve;
 a cover engaged on top of the container body for enclosing the open top of the container body, the cover comprising an air release valve in an upper portion of the cover above the container body and an interior cover sleeve structured to mate with the outer body sleeve with an air tight slide fit over the mating outer body sleeve so that it is necessary to open the air release valve to slide the cover onto the container body releasing air through the air release valve to create a vacuum seal, producing at least a partial vacuum in the container, with the cover fully installed on the container body and so that it is necessary to open the air release valve to admit air into the container to release the vacuum seal to enable the cover to be removed from the container body, wherein the air release valve further comprises:
 a channel formed in the cover and an air opening formed through the cover, the opening communicating with the channel so that air can pass through the channel into the container;
 a knob slidably engaged in the channel, the knob comprising a top portion for engaging the knob to activate the air valve, a hollow tube extended from the knob into the channel, the hollow tube having side wall openings, and at least one projection from the knob for engaging with the cover to prevent the knob from engaging into the channel;
 a bottom plug engaging the knob through the air opening, the bottom plug having a flat top surface for covering the air opening to block the air and a shaft extending upwardly from the bottom plug with an expanded partially tapered head on the top of the shaft, the shaft inserted through the air opening and into the hollow tube of the knob and the head snaps out into the side wall openings to lock the bottom plug to the knob through the air opening; and
 a biasing means biased between the knob and the plug for biasing the knob partially outward of the cover and for forcing the plug against the cover to normally seal the air opening through the cover to prevent air from passing therethrough until the plug is pushed by a user to release the plug and admit the air through the opening; and at least one protrusion on one side of the outer body sleeve, and at least one mating L-shaped opening on a bottom edge of the cover, one on each of two sides of the cover to mate with the protrusions so that as the cover is installed, while activating the air release valve, a vertical edge portion of the at least one L-shaped opening engages the mating protrusion and as the protrusion reaches a horizontal portion of the L-shaped opening the cover is turned to fully insert the protrusion in the horizontal portion to lock the cover onto the container to enable the container to be lifted by the cover, and the cover is turned in an alternate direction to align the vertical edge portion of the L-shaped opening with the protrusion and the cover lifted while activating the air release valve to remove the cover from the container body.

2. The vacuum sealed container of claim 1 wherein the outer body sleeve of the container comprises a tapered conical upper portion of a cylindrical sleeve around the open top of the container, narrower at a top portion adjacent to the open top to allow the cover to slip easily over a rim down onto a mating cylindrical portion wherein the air release valve is required to install the cover over an outer cylindrical portion of the container sleeve.

3. The vacuum sealed container of claim 2 further comprising a handle on the cover for maneuvering the cover onto and off of the container body, the handle positioned adjacent to the air release valve so that the air release valve may be activated by a hand of a user holding the handle and the handle on the cover is used to lift the container.

4. The vacuum sealed container of claim 2 wherein the cover comprises a hollow cylindrical tube having a flat top and the vacuum release valve on the side of the cover adjacent to the top so that a plurality of covered containers may be stacked on top of each other.

5. The vacuum sealed container of claim 1 wherein the biasing means comprises a spring.

6. The vacuum sealed container of claim 1 further comprising a rack for vertically stacking a plurality of the vacuum sealed containers each oriented horizontally in a vertical stacked array, the rack comprising a plurality of container supports, each container support comprising a pair of horizontally spaced mating cradles interconnected by a means for rigidly interconnecting the cradles, each of the cradles comprising an elongated member having a top surface for engaging and supporting a bottom of a vacuum sealed container and a bottom surface for resting on a top of a vacuum sealed container so that a container support is positioned under a bottom vacuum sealed container and between each adjacent vacuum sealed container in the vertical stacked array.

7. The vacuum sealed container of claim 6 wherein each of the container supports further comprises a container edge support protruding from a back edge of one of the cradles, the container edge support configured to receive and support a bottom edge of one of the vacuum sealed containers to prevent each vacuum sealed container from sliding off a back of the stacked array so that the covers may be installed on and removed from the vacuum sealed containers to access contents of the vacuum sealed containers while remaining in the vertical stacked array.

* * * * *